United States Patent [19]

Goldin et al.

[11] Patent Number: 5,438,130
[45] Date of Patent: Aug. 1, 1995

[54] FUCOSYLATED GUANOSINE DISULFATES AS EXCITATORY AMINO ACID ANTAGONISTS

[75] Inventors: Stanley Goldin, Lexington; James Fisher; Kazumi Kobayashi, both of Arlington; Laxma Reddy, Malden; Andy Knapp, Salem; Lee Margolin, Belmont, all of Mass.; Kevin D. McCormick, Ithaca, N.Y.

[73] Assignees: Cambridge NeuroScience, Inc., Cambridge, Mass.; Cornell Research Foundation, Inc., Ithaca, N.Y.

[21] Appl. No.: 4,928

[22] Filed: Jan. 15, 1993

[51] Int. Cl.$^6$ ............................................. C07H 19/167
[52] U.S. Cl. .................................. 536/27.81; 514/45; 536/26.3; 536/26.7
[58] Field of Search ....................... 536/27.81; 514/45

[56] References Cited

U.S. PATENT DOCUMENTS

| | | | |
|---|---|---|---|
| 4,770,994 | 9/1988 | Rittenhouse | 435/7 |
| 5,180,674 | 1/1993 | Roth | 435/288 |
| 5,210,078 | 5/1993 | Toyokuni et al. | 514/54 |

OTHER PUBLICATIONS

Zivin et al., "Stroke Therapy," *Scientific American*, 265(1), 56–63 (Jul. 1991).
Khilanani et al., "Guanosine Diphosphate–L–Fucose Plasma: N-Acetylglucosaminide Fucosyltransferase as in Index of Bone Marrow Hyperplasia After Chemotherapy," *Cancer Res.*, 38(1), 181–184 (1978).
Koscielak et al., "Activities of Fucosyltransferases in Sera of Leukemia Patients; Platelet Origin of Serum α-6-L-Fucosyltransferase," *Biochem. Soc. Trans.*, 15(4), 603–606 (1987); *Chem. Abstr.*, 107(9), p. 498, Abstr. No. 75389v (1987); only Abstract provided.
A. Scriabine, "Pharmacology of Nimodipine-A Review," *Adv. in Neurosurgery*, 18, 173–179 (1990).
Price et al., "Excitatory Amino Acid Antagonists as Anti-Emetics," *Soc. Neuroscience Abstr.*, 16, 377, Abstr. No. 161.14 (1990).

Wong et al., "Calcium Antagonists: Stroke Therapy Coming of Age," *Stroke*, 21(3), 31–36 (1990).
Ginsberg et al., "Rodent Models of Cerebral Ischemia," *Stroke*, 20(12), 1627–1642 (1989).
D. W. Choi, "Methods for Antagonizing Glutamate Neurotoxicity," *Cerebrovascular Brain Metabol. Rev.*, 2, 105–147 (1990).
D. W. Choi, "Glutamate Neurotoxicity and Diseases of the Nervous System," *Neuron*, 1, 623–634 (1988).
Dreyer et al., "HIV-1 Coat Protein Neurotoxicity Prevented by Calcium Channel Antagonists," *Science*, 248, 364–367 (1990).
Suszkiw et al., "Further Characterization of Phasic Calcium Influx in Rat Cerebrocortical Synaptosomes: Inferences Regarding Calcium Channel Type(s) in Nerve Endings," *J. Neurochem.*, 52(4), 1260–1269 (1988).
Suszkiw, "Properties of Presynaptic Voltage-Sensitive Calcium Channels in Rat Synaptosomes," *NATO ASI Series, H21*, 285–291 (1988).
Turner et al., "Calcium Channels in Rat Bain Synaptosomes: Identification and Pharmacological Character- (List continued on next page.)

*Primary Examiner*—Douglas W. Robinson
*Assistant Examiner*—L. Eric Crane
*Attorney, Agent, or Firm*—Gregory B. Butler

[57] ABSTRACT

A compound consisting of a base, a ribose and a fucose, in which the base is a purine or a pyrimidine, the ribose has $R_1$ and $R_2$ attached respectively to any two of 2'-O, 3'-O and 5'-O, and the fucose has $R_3$, $R_4$ and $R_5$ attached respectively to any three of 1"-O, 2"-O, 3"-O and 4"-O, wherein each $R_1$, $R_2$, $R_3$, $R_4$ and $R_5$ is H, acetate, sulfate, phosphate, or a metallic salt of acetate, sulfate or phosphate; and the base is linked to the ribose via a bond between 9-N of the base and 1'-O of the ribose when the base is a purine or via a bond between 1-N of the base and 1'-C of the ribose when the base is a pyrimidine and the ribose is linked to the fucose via a bond between any one of 2'-O, 3'-O and 5'-O of the ribose and 1"-C of the fucose.

38 Claims, 14 Drawing Sheets

OTHER PUBLICATIONS ization. High Affinity Blockade by Organic $Ca^{+2}$ Channel Blockers," *J. Neurosci.*, 5(3), 841–849 (1985).

Bean, "Classes of Calcium Channels in Vertebrate Cells," *Ann. Rev. Physiol.*, 51, 367–384 (1989).

Nowycky et al., "Three Types of Neuronal Calcium Channel with Different Calcium Agonist Sensitivity," *Nature*, 316, 440–443 (1985).

Gelmers et al., "A Controlled Trial of Nimodipine in Acute Ischemic Stroke," *New Engl. J. Med.*, 318(4) 203–207 (1988).

Fink-Jensen et al., "Inhibition of Cisplatin-Induced Emesis in Ferrets by the Non-NMDA Receptor Antagonists NBQX and CNQX," *Neurosci. Lett.*, 137 173–177 (1992).

MacDermott et al., "NMDA-Receptor Activation Increases Cytoplasmic Calcium Concentration in Cultured Spinal Cord Neurones," *Nature*, 321, 519–522 (1986).

Watkins et al., "Agonists and Antagonists for Excitatory Amino Acid Recptors," *Trends in Neurosciences*, 10(7), 265–272 (1987).

Albers et al., "N-Methyl-D-Aspartate Antagonists: Ready for Clinical Trial in Brain Ischemia," *Ann. Neurol.*, 25, 398–403 (1989).

Eberhard et al., "Galactopyranosyl-$\beta$(1->3)-ribonucleosides-Structural Evidence and Synthesis," *Nucleic Acids Research Sympos. Ser.*, (9), 15–19 (1991).

Shimofuridin A, a "Nucleoside Derivative Embrasing an Acylfucopyranoside Unit Isolated from the Okinawan Marine Trunicate *Aplidimmultiplicatum*," *J. Org. Chem.*, 59, 255–257 (1994).

Huber, "Esters of Adenosine with Organic and Inorganic Acids," *Chem. Ber.*, 89, 2853–2862, (1956); *Chem. Abstr.*, 52(3), 2028b (1958); only Abstr, supplied.

FUCOSYLATED GUANOSINE DISULFATES AS EXCITATORY AMINO ACID ANTAGONISTS

STATEMENT AS TO FEDERALLY SPONSORED RESEARCH

This invention was made with support from National Institutes of Health, National Institute of General Medical Sciences, Grant No. GM41547. Accordingly, the U.S. Government has certain rights in the invention.

FIELD OF THE INVENTION

The invention relates to a class of compounds which have affinity for neurotransmitter receptors.

BACKGROUND OF THE INVENTION

Because neurons of the mature central nervous system ("CNS") are highly specialized and in general do not replace themselves, death or degeneration of cells in the nervous system has far more serious consequences than it does in other organs. Abnormal neuronal death can be rapid and widespread as in traumatic brain injury, or can occur over many years among very specific populations of neurons as in chronic neurodegenerative diseases.

Despite this diversity, substantial evidence now points to pernicious overactivity of normal neurotransmitter systems as a contributory mechanism in many instances of pathological neuronal degeneration. In particular, overstimulation of neuronal receptors for L-glutamate, the brain's most prevalent excitatory amino acid ("EAA") neurotransmitter, is now well established as a causal or exacerbating factor in several acute neurological disorders, and has been proposed to underlie a number of chronic neurodegenerative diseases as well [Choi, D. W., Neuron 1:623 (1988); Choi, D. W., Cerebrov. and Brain Metab. Rev. 2:105 (1990); and Albers, G. W. et al. Ann. Neurol. 25:398 (1989)].

In the mammalian brain, glutamate interacts with three major classes or receptors, i.e., N-methyl-D-aspartate ("NMDA") receptors, non-NMDA receptors and metabotropic receptors [Watkins, J. C. et al., Trends Neurosci. 10:265 (1987)]. While triggering distinctive postsynaptic responses, all three classes of glutamate receptors can act to increase the intracellular concentration of free $Ca^{2+}$ in nerve cells [MacDermott, A. B. Nature 321:519 (1986)]. Thus, binding of glutamate to the NMDA receptor opens a cation-selective channel that is markedly permeable to $Ca^{2+}$, leading to a large and rapid increase in intracellular $Ca^{2+}$. Although non-NMDA receptors are in most instances linked to cation channels that largely exclude calcium, they can indirectly promote $Ca^{2+}$ entry into neurons by depolarizing the cell membrane, which in turn opens voltage-activated $Ca^{2+}$-channels The so-called "metabotropic receptor" on the other hand, is not associated with an ion channel but can promote the release of $Ca^{2+}$ from intracellular stores via the second-messenger inositol triphosphate.

Irrespective of the triggering mechanism, prolonged elevation of cytosolic $Ca^{2+}$ is believed to be a key event in the initiation of neuronal destruction. Adverse consequences of elevated intracellular $Ca^{2+}$ include derangement of mitochondrial respiration, activation of $Ca^{2+}$-dependent proteases, lipases and endonucleases, free radical formation and lipid peroxidation of the cell membrane.

There are few effective treatments for excitotoxic pathologies. In recent years, much effort has been directed at developing antagonists of glutamate receptors as potential neuroprotective agents. To date, most of this research has focused on devising antagonists of the NMDA receptors and/or their associated ion channels. NMDA receptors are an attractive therapeutic target because they can be antagonized noncompetitively via a number of different pharmacological binding sites as well as competitively at the glutamate recognition site. Concern about possible behavioral and other CNS side effects of NMDA antagonists has led to an emphasis on using these drugs only to treat acute disorders.

Non-NMDA receptors constitute a broad category of postsynaptic receptor sites which, as is the case for NMDA receptors, are directly linked to ion channels. Specifically, the receptor sites are physically part of specific ion channel proteins. Non-NMDA receptors have been broadly characterized into two major subclasses based on selectively for the aforementioned compounds: kainate receptors and AMPA/quisqualate receptors [see Watkins, J. C. et al., Trends Neurosci. 10:265 (1987)]. AMPA is an abbreviation for $\alpha$-amino-3-hydroxyl-5-methyl-4-isoazole propionic acid. These two subclasses may overlap substantially in their pharmacology, and in their relationship to neuronal function and pathology. We will thus broadly categorize these subclasses as "non-NMDA" receptors, and present evidence that the compounds claimed block postsynaptic responses to both kainate and quisqualate.

Compared to NMDA receptors, non-NMDA receptors have received less pharmacological scrutiny—the existing antagonists are all competitive—and in vivo research in this area has been hampered by the lack of drugs that cross the blood-brain barrier. Nonetheless, in vivo studies have clearly demonstrated that non-NMDA receptor agonists can be as excitotoxic as NMDA agonists, although longer exposures are required. In addition, evidence from animal studies and from human epidemiological studies suggests that excitotoxicity mediated by non-NMDA receptors may be clinically important in certain pathologies [Ginsberg, M. D., et al. Stroke 20:1627 (1989)].

One such disorder is global cerebral ischemia, as occurs following cardiac arrest, drowning, and carbon monoxide poisoning. Transient, severe interruption of the cerebral blood supply in animal causes a syndrome of selective neuronal necrosis, in which degeneration occurs among special populations of vulnerable neurons (including neocortical layers 3,5 and 6, pyramidal cells in hippocampal zones CA1 and CA3, and small and medium sized striatal neurons). The time course of this degeneration is also regionally variable, and can range from a few hours (striatum) to several days (hippocampus).

NMDA antagonists have generally not proven effective in animal models of global ischemia; indeed, it has been suggested that positive results obtained using NMDA antagonists may largely be artifactual. In contrast, the competitive kainate antagonist 2,3-dihydroxy-6-nitro-7-sulfamoyl-benzo(F)quinoxaline ("NBQX") is dramatically effective in preventing delayed neuronal degeneration following transient forebrain ischemia in both gerbils and rats. Importantly, protection was observed even when NBQX was administered several hours after the ischemic insult. These experiments used relatively large systemic doses of NBQX; evidently this compound crosses the blood-brain barrier only in minute amounts. Thus, there is an urgent need for additional antagonists.

Kainate receptor-mediated excitotoxicity may also play a role in chronic neurological disorders, although the evidence on this point is indirect. It is known that ingestion of some naturally occurring excitatory amino acid agonists can cause symptoms reminiscent of neurodegenerative diseases. These include the cycad plant toxin β-N-methylamino-L-alanine, a possible cause of Guam amyotrophic lateral sclerosis/Parkinsonism-dementia ("ALS/PD"); the chick-pea toxin β-N-oxalylamino-L-alanine, implicated in the etiology of lathyrism; and the mussel toxin domoic acid, whose ingestion causes paralysis and memory impairment. The similarity of these conditions to spontaneously occurring neurodegenerative diseases has led to a proposal that ALS/PD and Alzheimer's disease may involve an excitotoxic component [see Choi, D. W., Neuron 1:623 (1988); and Choi, D. W., Cerebrov. and Brain Metab. Rev. 2:105 (1990)].

It has recently been reported that NMDA antagonists which do not cross the blood/brain barrier may be used to alleviate certain undesirable side effects of cancer chemotherapy, e.g. nausea and emesis [Fink-Jensen, A. et al. Neurosci. Lett. 137(2):173 (1992)]. Because the compounds claimed herein are charged and quite hydrophilic, it may be the case that such compounds have difficulty in crossing the blood/brain barrier. Accordingly, we propose that HF7 discovered by us and its derivatives (see below), being hydrophilic NMDA antagonists with limited blood brain barrier permeability, can be used clinically to ameliorate the side effects of cancer chemotherapy, and chemotherapy in general.

Price, M. T. et al. Soc. Neurosci. Abstr. 16:377, abstr. 161.16 (1990), discloses that the administration of EAA antagonists completely prevented emesis in ferrets that were subject to chemotherapy with cisplatin. The EAA antagonists employed did not penetrate the blood-brain barrier, and it was thus suggested that such compounds may prevent nausea, a common side effect during cancer chemotherapy.

Calcium antagonists such as nimodipine act both as cerebral vasodilators and as calcium channel blockers in neurons [see Wong, M. C. W. et al. Stroke 24:31 (1989) and Scriabine, A., Adv. Neurosurg (1990), respectively]. Modest improvement in the outcome of stroke has been observed in clinical trials [Gelmers, H. J. et al. N. Eng. J. Med. 318:203 (1988)]. While there are significant cardiovascular side effects, nimodipine appears less toxic than the NMDA antagonists and may find a role in the chronic treatment of stroke and other neurological disorders.

There are at least 4 subclasses of calcium channels, "T", "N", "L", and "P", that differ in their pharmacology, location in neuronal and non-neuronal tissues, and physiological properties [Nowycky, M. C. et al. Nature 316:440 (1985); Bean B. P. Ann. Rev. Physiol. 51:367 (1989)]. Voltage-sensitive calcium channels (VSCC) in presynaptic nerve terminals control the influx of $Ca^{2+}$ and thereby determine the quantity and duration of transmitter released by the presynaptic action potentials. Biochemical $^{45}Ca$ tracer flux experiments with isolated nerve endings (synaptosomes) indicate that K+-depolarization dependent $^{45}Ca$ entry consists of fast transient and slow sustained components. The transient calcium influx has been determined to represent a channel mediated process, whereas the sustained component reflects calcium entry via reversed Na/Ca exchange [Turner, T. et al. J. Neurosci. 5:841 (1985); Suskziw, J. B. NATO ASI Series, H21:286 (1988); Suszkiw, J. B. et al. J. Neurochem. 42:1260 (1989)].

European Patent Application No. 0 266 574, discloses that calcium overload blockers will be useful in the treatment of anoxia, ischemia, migraine and epilepsy. This application also discloses that certain piperidine derivatives have activity against calcium overload in the brain and may be used in the treatment of migraine.

Dreyer, E. B. et al., Science 248:364 (1990), discloses that the HIV-1 coat protein gp120 produces neuronal cell injury which may be responsible for the dementia and blindness encountered in acquired immunodeficiency syndrome. Calcium channel antagonists prevented the gp120-induced neuronal injury of retinal ganglion cells. Dreyer et al. propose that calcium channel antagonists may prove useful in mitigating HIV-1 related neuronal injury.

SUMMARY OF THE INVENTION

One aspect of the present invention relates to a class of novel nucleoside derivatives which are capable of binding to glutamate receptors.

Structurally, a compound of the invention consists of three moieties: a base, a ribose and a fucose. The base can be either a purine or a pyrimidine. The ribose has $R_1$ and $R_2$ attached respectively to any two of 2'-O, 3'-O and 5'-O, and the fucose has $R_3$, $R_4$ and $R_5$ attached respectively to any three of 1"-O, 2"-O, 3"-O and 4"-O wherein each $R_1$, $R_2$, $R_3$, $R_4$ and $R_5$ is H, acetate, sulfate, phosphate or a metallic salt of acetate, sulfate or phosphate. The three moieties are linked together as follows: the base is linked to the ribose via a bond between 9-N of the base and 1'-C of the ribose when the base is a purine or via a bond between 1-N of the base and 1'-C of the ribose when the base is a pyrimidine and the ribose is linked to the fucose via a bond between any one of 2'-O, 3'-O and 5'-O of the ribose and 1"-C of the fucose.

The structures and numbering systems of purine, pyrimidine, ribose and fucose are as follows:

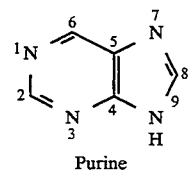

Purine

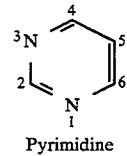

Pyrimidine

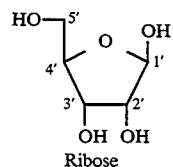

Ribose

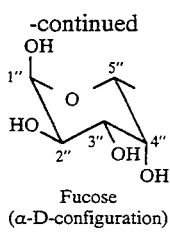

Fucose
(α-D-configuration)

Note that the term "purine" refers to both substituted purines (including adenine and guanine) and nonsubstituted purines. Similarly, a pyrimidine can be either a substituted pyrimidine (e.g., cytosine and thymine) or a nonsubstituted pyrimidine inclusive.

Also note that both the ribose and the fucose moieties of the compound can be of α-D-, α-L-, β-D-, or β-L-configuration.

Preferably, the base moiety of the compound is a purine, each $R_1$ and $R_2$ of the ribose moiety is sulfate, or one of $R_3$, $R_4$ and $R_5$ of the fucose moiety is acetate while each of the other two is H.

It is particularly preferred that the base moiety is of the following structure:

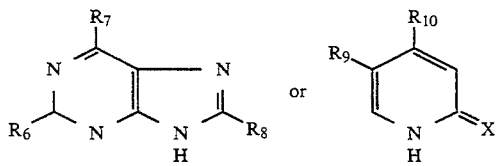

Each $R_6$, $R_7$, $R_8$, $R_9$, and $R_{10}$ can be independently H, hydroxy, acetate, alkyl, aryl, aralkyl, alkaryl, substituted aryl, alkoxy, amino, monoalkylamino, dialkylamino, aminoalkyl, halo, mercapto, acetate, carbamate, thioalkyl, alkanoyl, azido, acetamido, or sulfhydryl. X can be O, S, NH, or NR, where R is alkyl, alkoxy, carbamate, cyano, aryl, alkaryl, or aralkyl.

In general, alkyl groups (by itself, or in thioalkyl, dialkylamino, thioalkyl and the like) contain 1–6 carbon atoms, and can be in chain, branched, or cyclic form. Aryl groups, on the other hand, contain 6–12 carbon atoms either monocyclic or bicyclic in nature.

Typical alkyl groups are, for example, methyl, ethyl, propyl, isopropyl, butyl, isobutyl, tert-butyl, and hexyl, cyclopropyl, cyclopentyl, or cyclohexyl. Typically, aryl, alkaryl, aralkyl groups and substituted aryl groups thereof include benzyl, phenyl, 1-naphthyl, 2-naphthyl, biphenyl, o-, m- or p-tolyl, o-, m- or p-ethylphenyl, o or m-trifluoromethyl phenyl, 4-fluoro-3-ethyl phenyl, 3-nitrophenyl, 4-fluoro-3-nitrophenyl, or 3-azido phenyl.

The base moiety of the compound of the invention can be guanine, adenine, cytosine, thymine, uracil, hypoxanthine, 4-hydroxypyrazole [3,4-d] pyrimidine, 5-hydroxyuracil, 6-aza-2-thiouracil, 6-azauracil, 8-azidoadenine, $N^4$-benzoylcytosine, 6-benzylaminopurine, 6-chloropurine, $N^6$-butyryladenine, 8-bromoadenine, 2-chloropurine, 8-bromoguanine, 5-methyl-2-thiouracil, 3-methylthymine, 6-(methylthio)purine, 5-methylcytosine, 5-hydroxyuracil, 5-bromouracil, 5-fluorouracil, N-acetylcytosine, 5-azacytosine, 2-amino-6-chloropurine, 2-chloro-6-aminopurine, 2-amino-6-mercaptopurine, S-(2-hydroxy-5-nitrobenzyl)-6-thioguanine, and S-(2-hydroxy-5-nitrobenzyl)-6-thiohypoxanthine.

Preferred compounds include, but are not limited to, guanosine-3',5'-disulfate-2'-α-D-(4''-acetyl)fucose, guanosine-3',5'-disulfate-2'-β-D-(4''-acetyl)fucose, guanosine-3',5'-disulfate-2'-α-L-(4''-acetyl)fucose, guanosine-3',5'-disulfate-2'-β-L-(4''-acetyl)fucose, guanosine-2',5'-disulfate-3'-α-D-(4''-acetyl)fucose, guanosine-2',3'-disulfate-5'-β-D-(4''-acetyl)fucose, guanosine-2',5'-disulfate-3'-α-L-(4''-acetyl)fucose, guanosine-2',3'-disulfate-5'-β-L-(4''-acetyl)fucose, guanosine-3',5'-disulfate-2'-α-L-fucose; or guanosine-2'-α-L-fucose.

Also within the invention is the salt forms of the above-described compounds which include, but are not limited to, acetate, sulfate and phosphate or their metallic salts. e.g., disodium salt of guanosine-3',5'-disulfate-2'-α-L-fucose.

Another aspect of the present invention relates to a pharmaceutical composition including a therapeutically effective amount of a compound in a pharmaceutically acceptable carrier, the compound consisting of a base, a ribose and a aldohexose, in which the base is a purine or a pyrimidine, the ribose has $R_1$ and $R_2$ attached respectively to any two of 2'-O, 3'-O and 5'-O, and the aldohexose has $R_3$, $R_4$ and $R_5$ attached respectively to any three of 1''-O, 2''-O, 3''-O and 4''-O, wherein each $R_1$, $R_2$, $R_3$, $R_4$ and $R_5$ is H, acetate, sulfate, phosphate or a metallic salt of acetate, sulfate or phosphate; and the base is linked to the ribose via a bond between 9-N of the base and 1'-C of the ribose when the base is a purine or via a bond between 1-N of the base and 1'-C of the ribose when the base is a pyrimidine and the ribose is linked to the aldohexose via a bond between any one of 2'-O, 3'-O and 5'-O of the ribose and 1''-C of the fucose.

In the above-described pharmaceutical composition, it is preferred that the aldohexose is fucose, the base is purine, or each $R_1$ and $R_2$ is sulfate (or a sodium salt thereof). It is particularly preferred that the compound in the pharmaceutical composition be guanosine-3',5'-disulfate-2'-α-D-(4''-acetyl)fucose, guanosine-3',5'-disulfate-2'-β-D-(4''-acetyl)fucose, guanosine-3',5'-disulfate-2'-α-L-(4''-acetyl)fucose, or guanosine-3',5'-disulfate-2'-β-L-(4''-acetyl)fucose.

The dose of the compound of the present invention for treating the above-mentioned diseases varies depending upon the manner of administration, the age and the body weight of the subject and the condition of the subject to be treated, and ultimately will be decided by the attending physician or veterinarian. Such amount of the active compound as determined by the attending physician or veterinarian is referred to herein as a "therapeutically effective amount".

The formulations may conveniently be presented in unit dosage form and may be prepared by any of the methods well known in the art of pharmacy. All methods include the step of bringing the active ingredient(s) into association with the carrier which constitutes one or more accessory ingredients. In general, the formulations for tablets or powders are prepared by uniformly and intimately blending the active ingredient with finely divided solid carriers, and then, if necessary as in the case of tablets, forming the product into the desired shape and size.

The broad range of activity of the above-described compounds against voltage-gated and ligand gated channels offers certain practical advantages. Specifically, members of this compound series or derivatives thereof can be created, which possess selectivity directed towards a particular subclass of ligand- or voltage- activated ion channels (e.g., towards non-NMDA receptors).

Thus, also within the invention is a therapeutic method using any of the compounds described above for treating or preventing a disorder of the nervous system or for alleviating side-effects of chemotherapy. The pathophysiology of the disorder may involve excessive excitation of receptors for excitatory amino acids (e.g., excitatory neurotransmitter glutamate) or persistent/excessive entry of calcium into nerve cells or persistent/excessive elevation of intracellular calcium levels in nerve cells. The nerve can be located either within the central nervous system or within the peripheral nervous system. Disorders of the nervous system which can be treated or prevented by this method include those resulting from stroke, head or brain trauma, global ischemia, coronary artery bypass surgery, myocardial infarction, drowning, or cardiac arrhythmias.

The therapeutic method is made possible to the capability of the above-described compounds to (i) attenuate the activity of the ion channels associated with the NMDA subclass of glutamate receptors and with the non-NMDA subclasses of glutamate receptors (including both kainate subclass and AMPA/quisqualate subclass of glutamate receptors) and (ii) attenuate the activity of voltage-sensitive calcium channels (including L-type, N-type, P-type and presynaptic calcium channels).

Other features and advantages of the invention will be apparent from the following description of the preferred embodiments thereof, and from the claims.

BRIEF DESCRIPTION OF THE DRAWINGS

The drawings will first be described.

(FIG. 1: initial separation; FIG. 2: further purification to apparent homogeneity of a compound designated as "HF7".)

DESCRIPTION OF THE PREFERRED EMBODIMENTS

Purification of HF7 from Spider Venom

*Hololena curta* spiders were collected in Arizona, USA and milked by Spider Pharm, Black Canyon City, Ariz., using electro-stimulation, producing a crude venom preparation that was supplied to the inventors as a frozen solution. The venom was thawed on ice, aliquoted into appropriate portions, and kept at −80° C. until use.

HF7 was purified by HPLC, using a Beckman System Gold HPLC system (both analytical and preparative) and LDC Preparative HPLC Systems. As described below, two protocols were followed. The first one led to the discovery of a compound termed HF7, and the second one was subsequently used as a routine procedure for large scale preparation of the compound.

Figure 1:
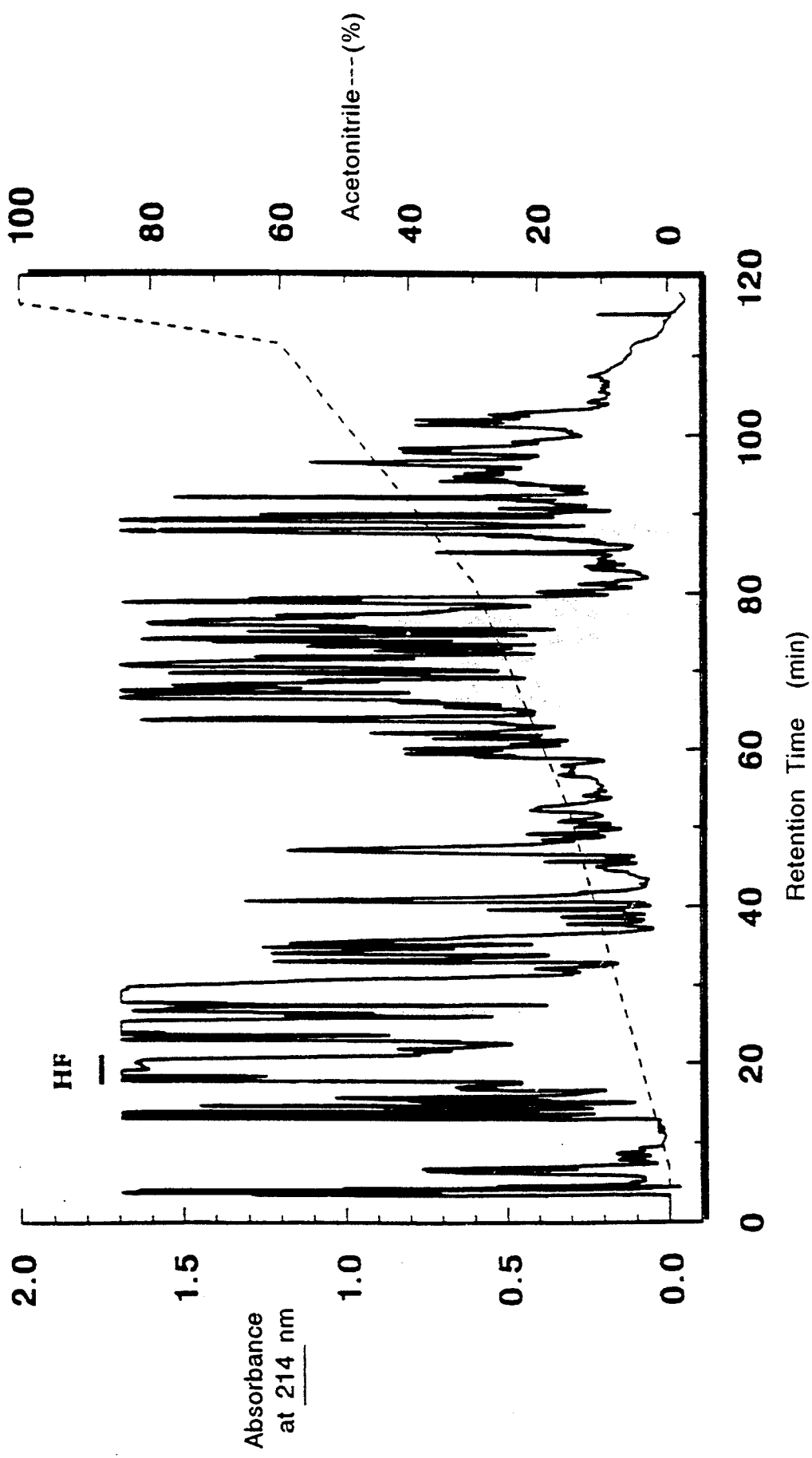
FIGS. 1 and 2 are elution profiles of *Hololena curta* venom fractionated by reverse phase high performance liquid chromatography ("HPLC"), illustrating absorbance of fractionated compounds at 214 nm versus time.

(1) Initial Purification for Screening (a) Identification of the HF fraction:

Crude venom (80 μl) was mixed with 160 μl of 0.1% trifluroacetic acid ("TFA") in H$_2$O and centrifuged at a room temperature for 5 min. at 13,000 rpm with an eppendorf microfuge. The supernatant was applied to a reversed-phase C18 HPLC column (100×250 mm, 5 μm, 100 Å), and HPLC was performed using an acetonitrile gradient of 0 to 60% in 0.1% TFA (FIG. 1) at a flow rate of 4.0 ml/min. The elution was monitored by absorbance at 214 nm (FIG. 1) and 254 nm, and the fractions were collected manually according to the elution profile. Each fraction was dried with a Speed Vac (Savant, Framingdale, N.Y.), suspended in 10 mM Tris-HCl Buffer (pH 7.3) containing 140 mM NaCl, 6.7 mM KCl, 2.4 mM CaCl$_2$, 1.3 mM MgCl$_2$, 11 mM Glucose and 0.004% H$_2$O$_2$ ("ACS"), and tested for its ability to block the dorsal root-ventral root reflex of hemisected spinal cords from new born-rats. The fraction was also subjected to [$^H$]-1-[1-(2-thienyl) cyclohexyl] piperidine ("TCP") , [$^3$H]-α-amino-3-hydroxy-5-methylsoxazole-4-propionate ("AMPA") and [$^3$H]-kainate binding assays. The fraction indicated in FIG. 1 as HF inhibited the spinal reflex nearly completely and inhibited [$^3$H]-TCP, [$^3$H]-AMPA and [$^3$H]-kainate binding by 80%, 50% and 68%, respectively.

(b) Further purification of the HF fraction

The HF fraction was prepared for further purification by following the method described above except that the fraction was identified by its elution profile instead of by assays. The first major peak with relatively high absorbance at 254 nm eluted with acetonitrile at a concentration about 9% was collected as the HF fraction, which was then dried, dissolved in 0.1% TFA of H$_2$O and applied to a C18 HPLC column (100×250 mm, 5 μm, 100 Å) equilibrated with 0.1% TFA.

Figure 2:
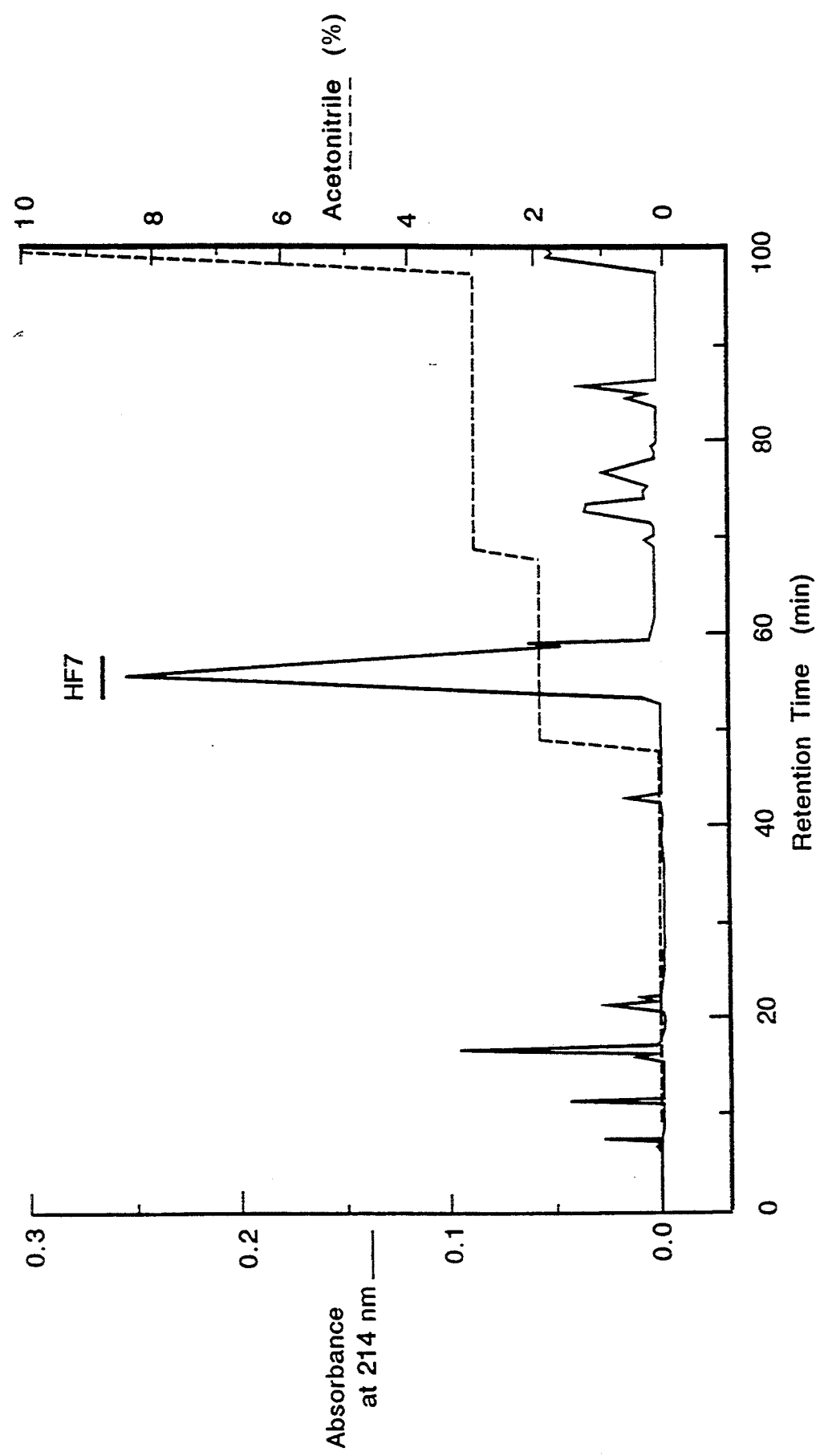

The components were eluted from the column stepwise with 0%, 2% and 4% acetonitrile in 0.1% TFA for the duration of 45 min., 15 min. and 40 min., respectively, at a flow rate of 2 ml/min. The elution was monitored by absorbance at 214 nm (FIG. 2) and 254 nm. According to the elution profile, fractions were collected manually and, after being dried down and dissolved in an appropriate buffer, were assayed in whole cell recording of glutamate-induced current under the voltage clamp mode (see "Functional Characterization" below for details). The major peak HF7, which constituted about 80% of the whole HF fraction, was found to be active. The other batch of HF7 was also purified with a slightly different program of acetonitrile stepwise elution (1% for 20 min., 2% for 20 min. and 4% for 40 min.), resulting in a shorter operation time without a significant change in the elution profile.

(c) Purity and functionality check of HF7

The purity of HF7 was confirmed by reversed-phase HPLC on a C18 analytical column (4.6×250 mm, 5 μm bead size, 100 Å pore size) using an acetonitrile gradient (0–50%) in 0.1% TFA at a flow rate of 1 ml/min. The purified HF7 was tested in various functional assays (see "Functional Characterization" below).

(2) Routine Large-Scale Purification Protocol

A 320 μl portion of frozen crude venom was thawed on ice and mixed with 60 μl of 0.1% TFA of H2O and centrifuged at a room temperature for 5 min. at 13,000 rpm with an eppendorf microfuge. The supernatant was applied to a reversed-phase C18 HPLC column (200×250 mm, 10 μm, 100 Å). HPLC was performed at a flow rate of 16 ml/min. using an acetonitrile gradient of 0% to 15% in 0.1% TFA over a 45 min. time span, followed by an increase of 15% to 30% in 30 min., and then an increase of 30% to 60% in 30 min. The elution was monitored by absorbance at 214 nm and 254 nm, and the fractions were collected manually according to the elution profile. The first major peak (based on the area in absorbance-time profile) was eluted with acetonitrile at a concentration about 9% and was collected as HF and dried down with a Speed Vac dryer.

The fraction was dissolved in 800 μl of 0.1% TFA in H2O, which was divided into four 200 μl aliquots. Each aliquot was reinjected for further purification onto a reversed-phase C18 HPLC column (200×250 mm, 10 μm bead size, 100 Å pore size, prepacked NGA column from The Nest Group, Southboro, Mass.). The HPLC was performed under isocratic conditions using 2.5% CH3CN (with 0.1% TFA) at 8 ml/min for 30 min. Elution was monitored by absorbance at 214 nm.

The major peak was collected as HF7 and dried down with a Speed Vac. The identity of this fraction as HF7 was confirmed by the coinjection of this fraction and previously purified HF7 onto the analytical C18 HPLC column.

Functional Characterization (I) Displacement of [$^3$H]-kainate by HF7

Figure 3:
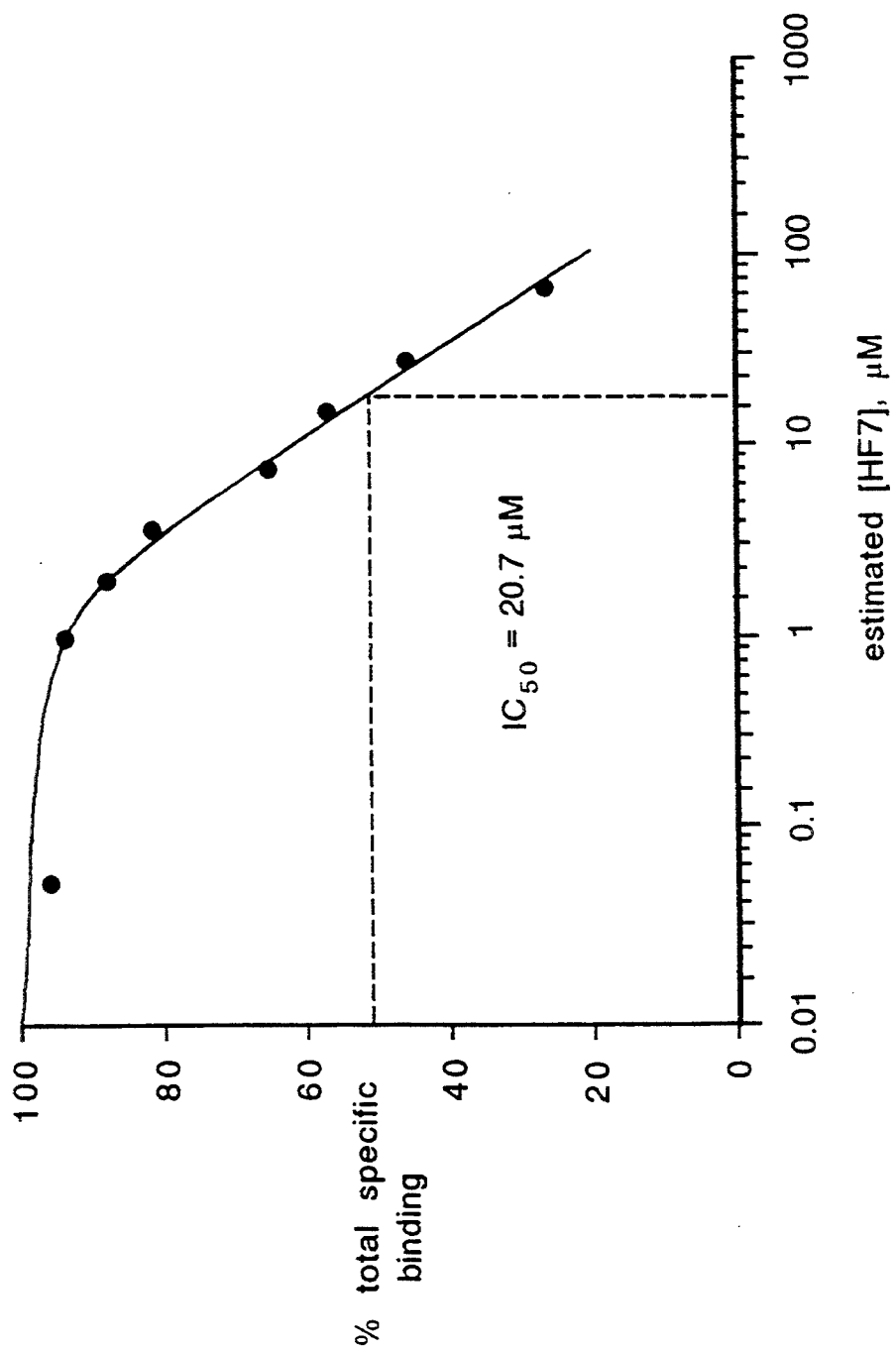
FIG. 3 is a graph showing inhibition of [$^3$H]-kainate binding as a function of HF7 concentration.

The ability of HF7 to block the kainate receptor was tested using a [$^3$H]-kainate binding assay. More specifically, a standard receptor binding assay [London, E. D. et al. Molecular Pharmacol. 15:492 (1979)] was performed to determine the extent to which HF7 could displace the binding of radioactive kainate ([$^3$H]-kainate, 1.0 mCi/ml, NEN). The membrane source was frozen rat forebrain crude synaptic membranes treated with detergent (0.01% TRITON-X100). Radioligand binding was determined using 50 mM Tris-acetate buffer. Samples were incubated for 1 hour at 4° C. and then filtered over either Whatman GF/B or Schleicher & Schuell glass filters. Non-specific binding was determined using $10^{-4}$M glutamate. [$^3$H]-kainate binding was linear from 50–400 μg protein/tube. The binding curve seen in FIG. 3 demonstrates that HF7 displaces [$^3$H]kainate binding with an approximate IC$_{50}$ of 20.7μM. For comparison, CNQX and DNQX, the most potent available non-NMDA antagonists, have IC$_{50}$'s near 2μM.

(II) The effect of HF7 on kainate currents in fish horizontal cells

In voltage clamp experiments on fish retinal neurons following the method described in Perlman, I. et al. Brain Res. 487:16 (1989), hereby incorporated by reference, it was observed that HF7 reversibly inhibited ionic currents elicited by glutamate (50μM), kainate (25μM) and quisqualate (10μM) in a dose-dependent manner.

Figure 4:
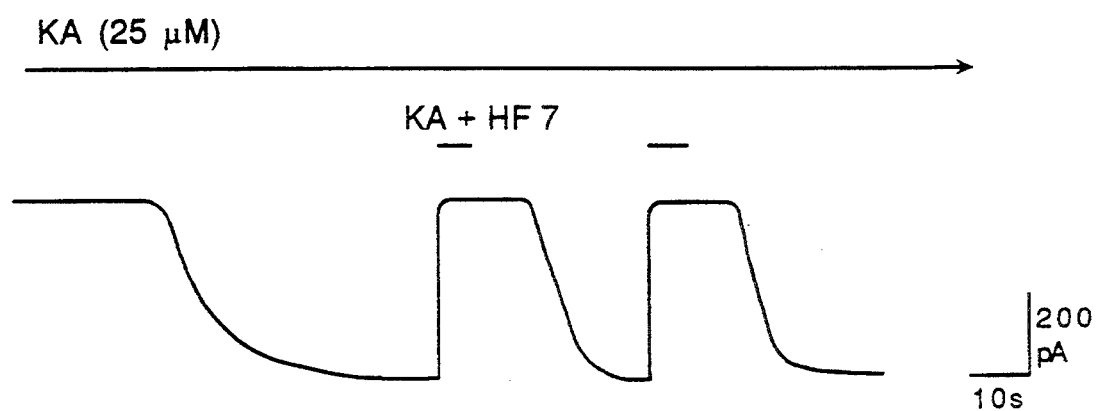
FIG. 4 is a graph showing near-complete inhibition of kainate-induced symptic current by ~200μM HF7 in voltage clamped retinal neurons of fish.

The results from one experiment showed near-complete inhibition of the kainate response by ~200μM HF7 (see FIG. 4). In this experiment, kainate currents were obtained from primary cultures of fish retinal horizontal cells using standard whole cell voltage clamp techniques [Hamill, O. P. et al. Pflugers Archives 391:85 (1981)]. For recordings cells were maintained in a physiological saline containing (in mM) NaCl, 145; KCl, 2.5; CaCl$_2$, 2.5; MgSO$_4$, 1.0; glucose, 10; HEPES, 10, pH 7.5). Cells were held near resting potential ($V_h$=−60 mV). Kainate current was elicited by superfusion of a solution of physiological saline solution containing 25μM kainate. Superfusion of the kainate elicited an inward current of ~400 pA, which was virtually eliminated by pressure-ejection (6 psi) of approximately 180μM HF7. The effects of HF7 blockade were fully reversible subsequent to washout.

Figure 5:
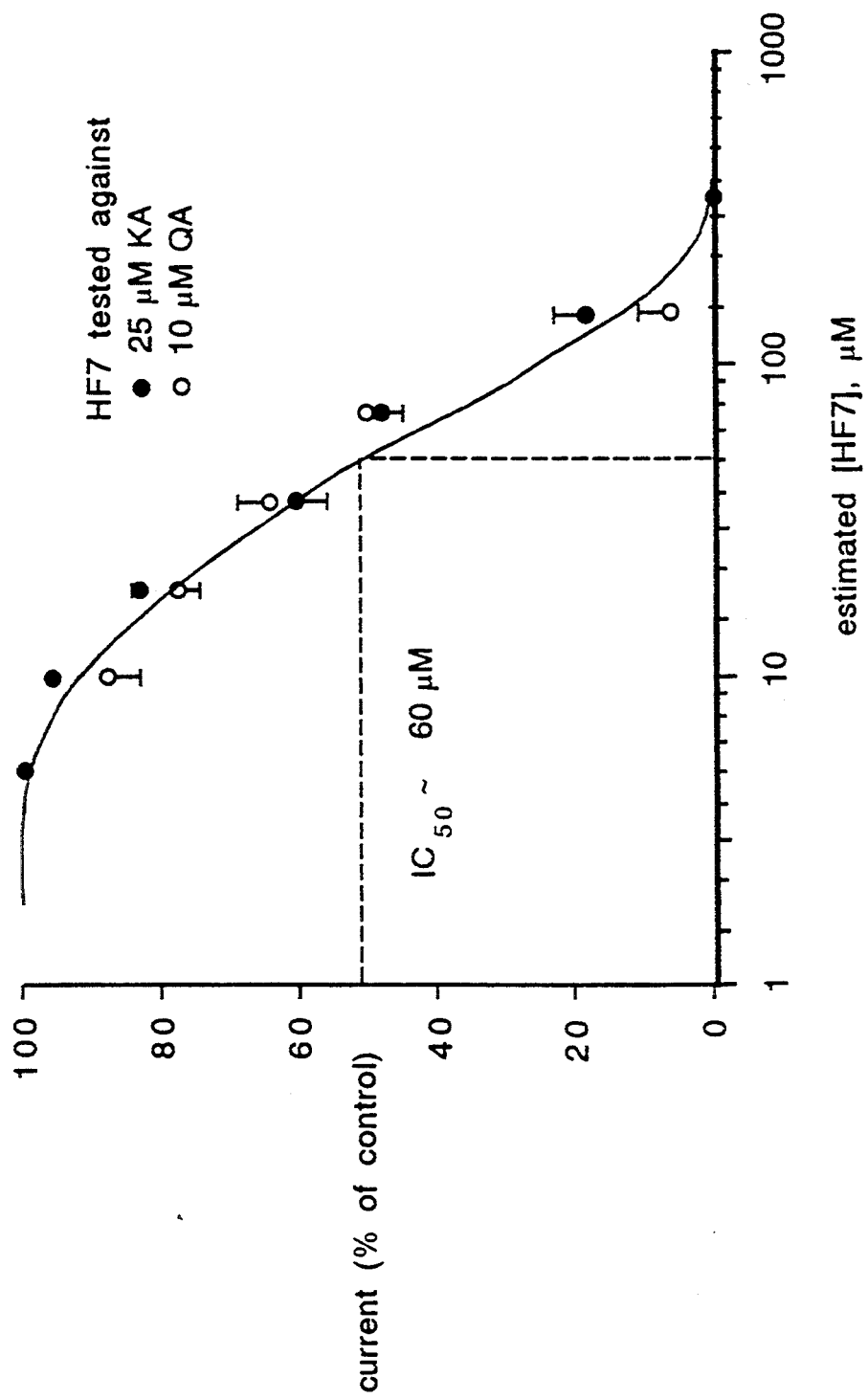
FIG. 5 is a graph showing inhibition of kainate receptors as a function of HF7 concentration in voltage clamped retinal neurons of fish.

(III) Concentration dependence of HF7 on kainate and quisqualate currents in fish horizontal cells Two sets of experiments were conducted to determine the concentration dependence of both kainate and quisqualate currents to HF7. Each experiment was conducted in a manner similar to that in which the FIG. 4 experiment was conducted. Inward currents were elicited by bath perfusion of either 25μM kainate or by 10μM quisqualate. Six doses of HF7 were utilized for each set of experiments. Each dose was tried on three different cells. Responses to HF7 were calculated as a percent of control kainate current. As can be seen in FIG. 5, the dose responses for kainate (solid circles) and quisqualate (open circles) were very similar; each was characterized by an IC$_{50}$ of approximately 60μM. Each point in FIG. 5 is the mean of measurement from three different cells.

(IV) Effect of HF7 on L-type calcium currents in N1E-115 murine neuroblastoma cells L-type calcium currents were obtained from cultured N1E-115 murine neuroblastoma cells using standard whole cell voltage clamp techniques [Hamill, O. P. et al. Pflugers Archives 391:85 (1981)]. For recording inward currents, external calcium was substituted with barium. Cells were maintained in a external recording solution containing TEA.Cl, 130 mM; BaCl$_2$, 5 mM; glucose, 10 mM; HEPES, 10 mM; tetrodotoxin, 1μM; pH 7.4). The pipette solution contained CsCl, 115 mM; EGTA, 10 mM; HEPES, 10 mM; Mg.ATP, 4 mM.

Figure 6:
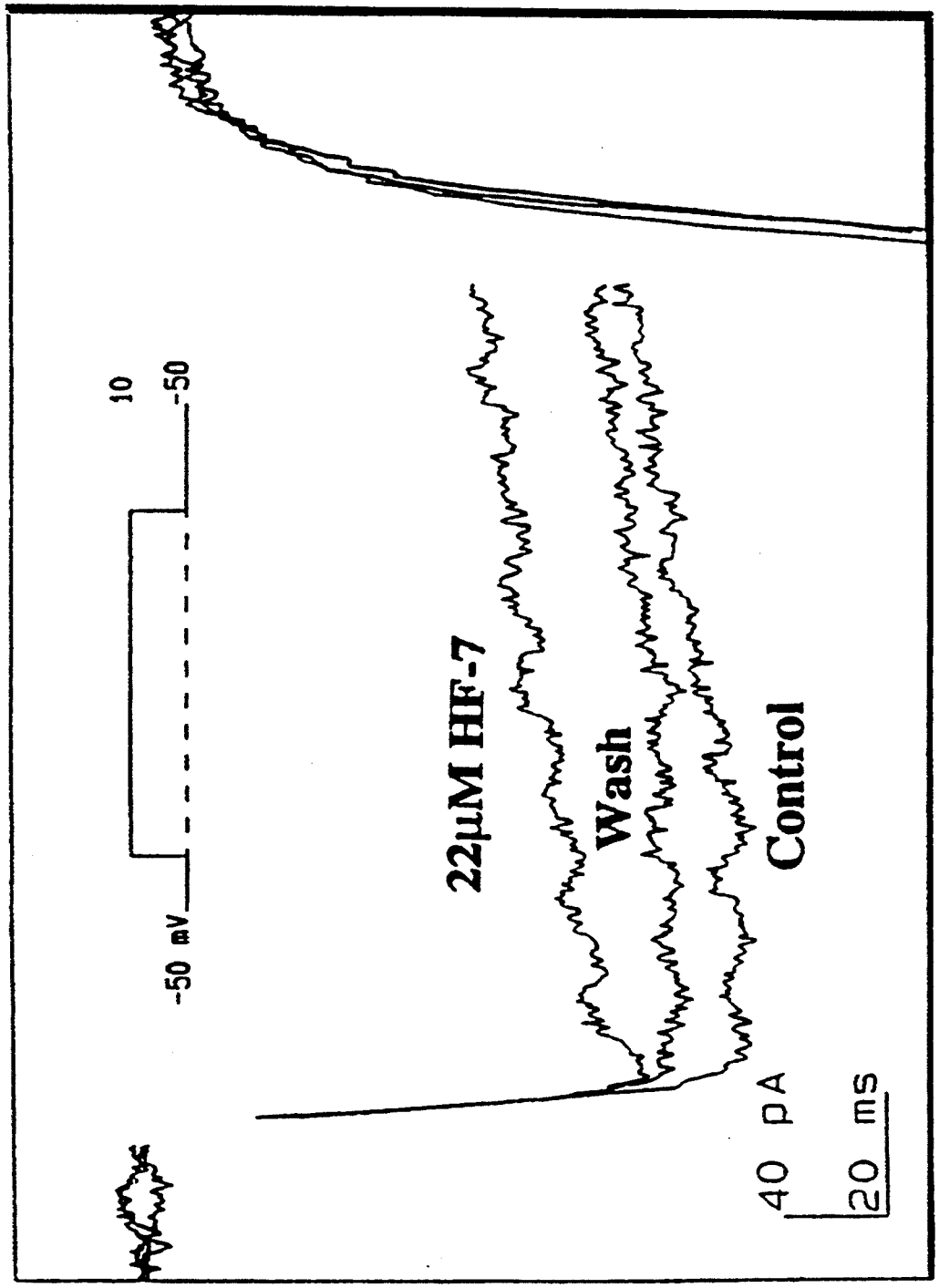
FIG. 6 is a graph showing effect of HF7 on L-type calcium currents in N1E-115 murine neuroblastoma cells.

The results from one experiment can be seen in FIG. 6. A depolarizing test pulse to +10 mV elicited an inward current of ~240 pA, which was reduced by 20% by pressure-ejection (6 psi) of 22μM HF7. The effects of HF7 blockade were partially reversible (60% recovery) subsequent to washout of HF7. The voltage protocol is shown in the inset. Cells were held at $V_h$=−50 mV. L-type currents were evoked following a depolarizing voltage step to +10 mV.

(V) Concentration dependence of HF7 on L-and T-type calcium currents in N1E-115 murine neuroblastoma cells Two sets of experiments were conducted to determine the concentration dependence of both L- and T-type calcium currents to HF7. Each experiment was conducted in a manner similar to that in which the FIG. 6 experiment was performed. Inward L-type currents were elicited by depolarizing test pulses to +10 mV from a resting potential of −50 mV. Inward T-type currents were elicited by depolarizing test pulses to −25 mV from a resting potential of −90 mV. Six doses of HF7 were utilized for each set of experiments. Each dose was tried on three different cells. Responses to HF7 were calculated as percent inhibition of control current. Negative values represent current levels that were greater than control.

Figure 7:
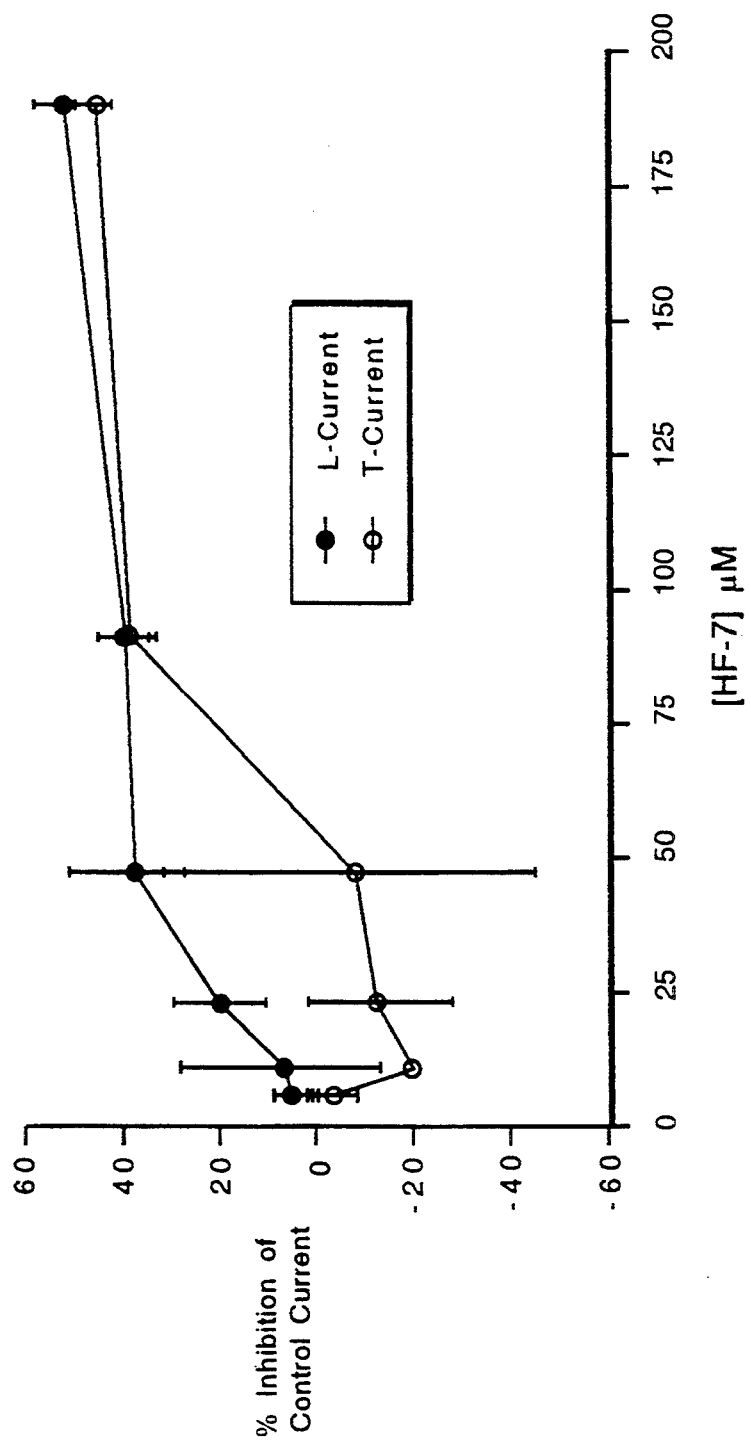
FIG. 7 is a graph showing concentration dependence of HF7 on L-and T-type calcium currents in N1E-115 murine neuroblastoma cells.

The results showed that throughout the concentration range used, L-type current was inhibited in a concentration dependent manner with little variation between trials of the same concentration (see FIG. 7). The effect of HF7 on T-type current, on the other hand, was much more variable, especially at concentrations between 0 and 90μM (also see FIG. 7).

Structural Elucidation of HF7

The amino acid analysis of purified HF7 sample showed only trace levels of standard amino acids (presumably derived from contaminants), suggesting that HF7 is not a peptide.

Figure 8:
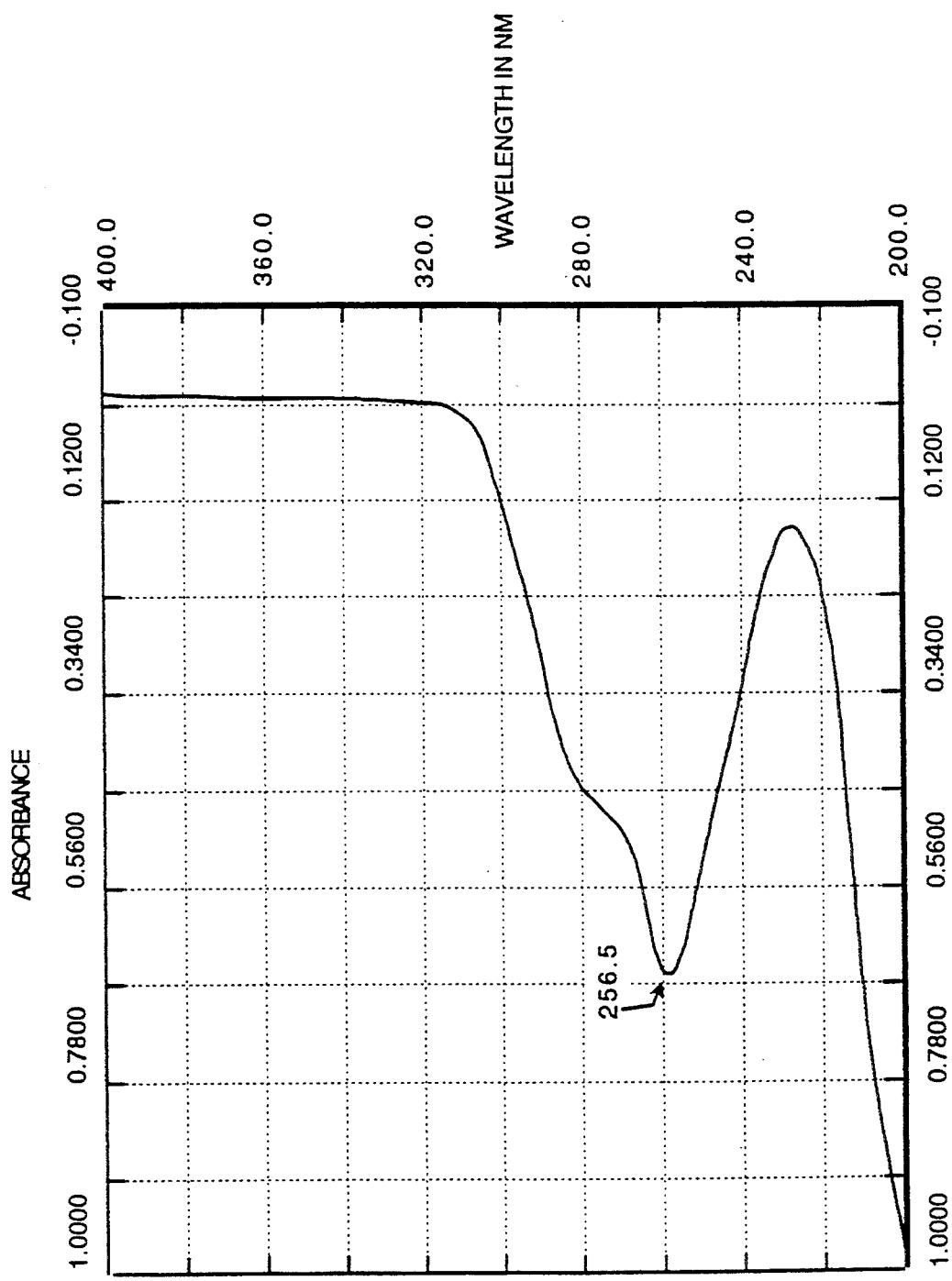
FIG. 8 is a UV spectrum of HF7.

The UV spectrum of HF7, shown in FIG. 8, was very similar to that of guanosine monophosphate ("GMP"), suggesting that HF7 is a nucleotide derivative.

Figure 9:
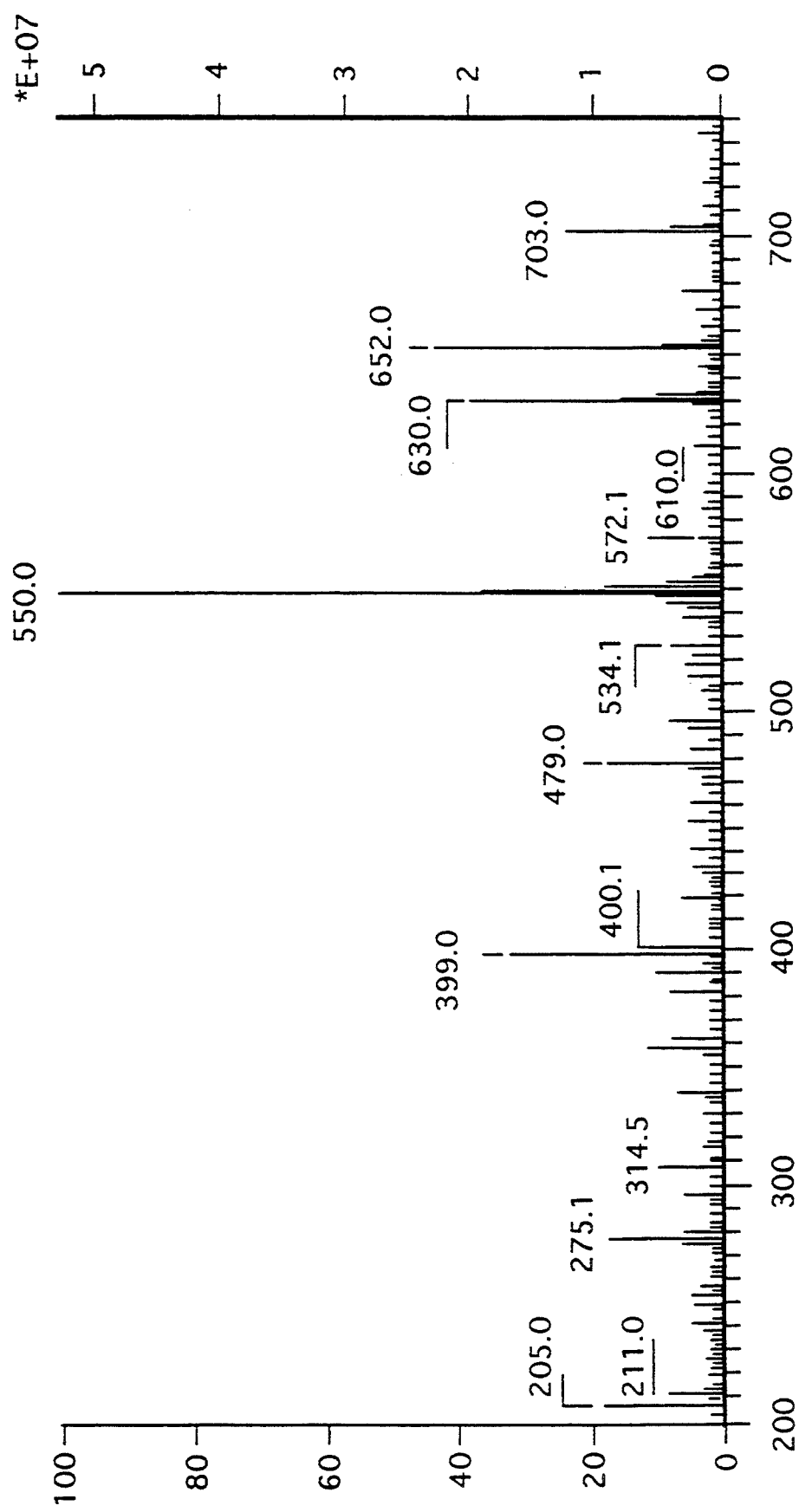
FIG. 9 is a negative ion fast atom bombardment ("FAB") mass spectroscopy of HF7.

The negative ion fast atom bombardment ("FAB") mass spectroscopy results revealed a peak at m/z=630 corresponding to (M—H)−, see FIG. 9. The peak at m/z=550 can be interpreted for the loss of SO₃, whereas the peak at m/z=479 appeared to be for the loss of guanine base. A peak at m/z=652 can be interpreted for M—2H⁺+Na⁺ which probably resulted from two negatively charged SO₃ groups closing together and thereby both capable of holding the Na⁺. There were peaks (m/z) corresponding to fucose-ribose unit with OAc, fucose-ribose unit without two SO₃ groups and fucose-ribose unit without OAc and two SO₃ groups. From the above mass spectral analysis, the molecular weight of HF7 was estimated to be m/z=631.

Figure 10:
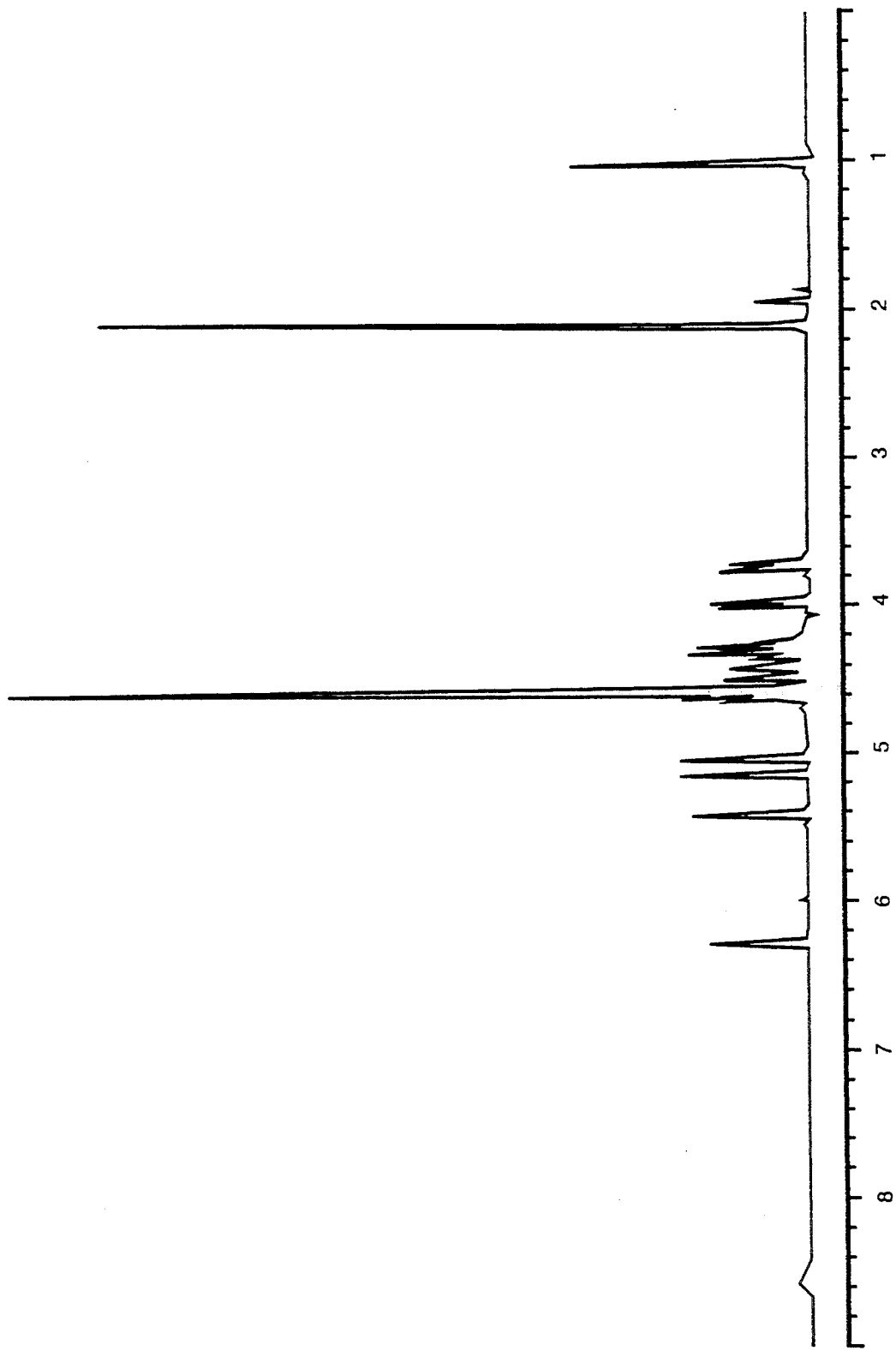
FIG. 10 is a $^1$H NMR spectrum of HF7.
Figure 11:
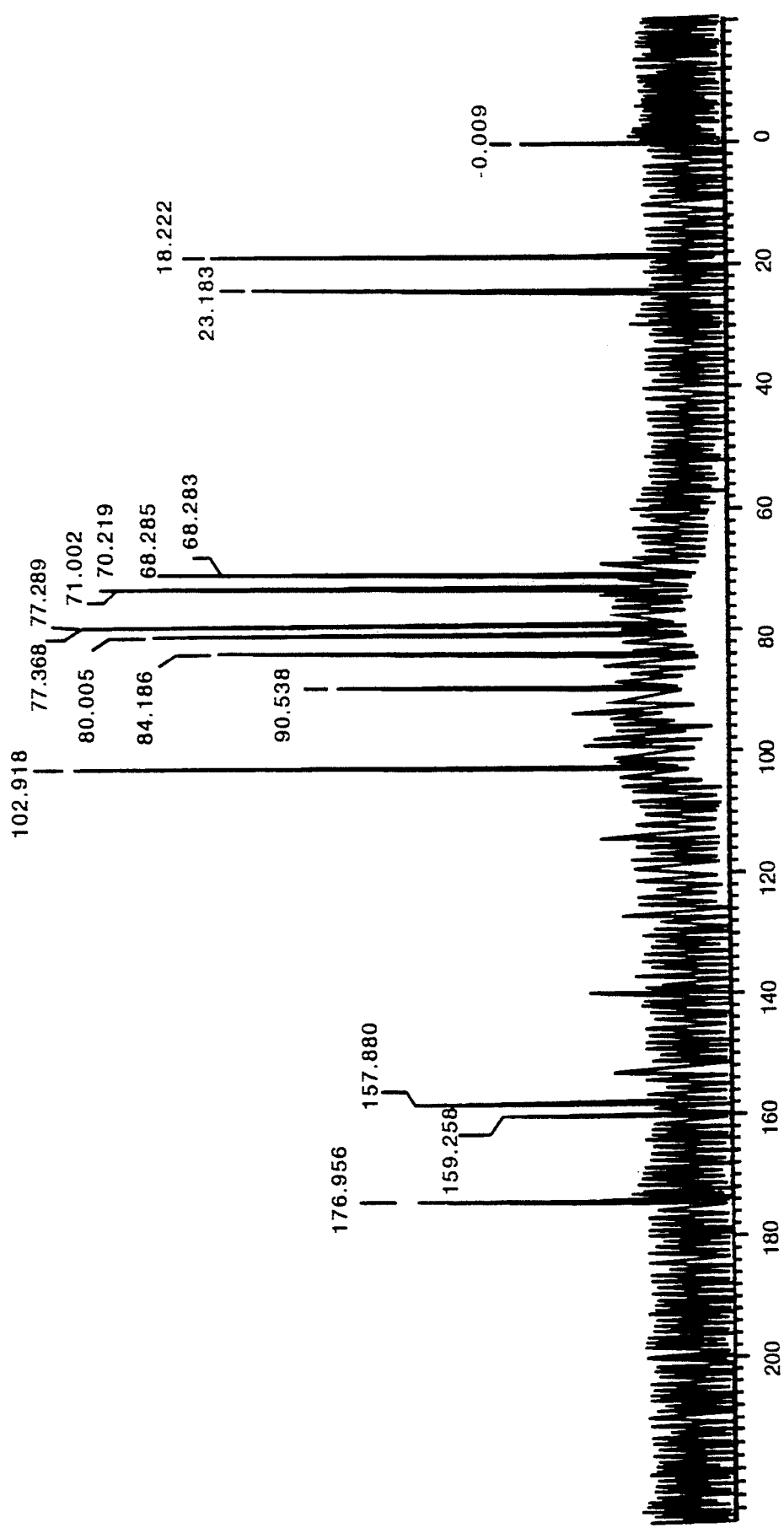
FIG. 11 is a $^{13}$C-NMR spectrum of HF7.

The guanine, fucose and ribose units were characterized from the NMR spectroscopy. The ¹H NMR spectrum of HF7 indicated eighteen non-exchangeable carbon bound protons and one CH₃ group attached to a CH carbon and one acetate group (see FIG. 10). The ¹³C-NMR spectrum showed eighteen carbon signals (see FIG. 11). However, no signals were observed in ³¹P-NMR study indicating that there are no phosphate groups in the molecule.

The information from NMR studies including 2-D ¹H NMR, ¹H—¹H decoupling, negative ion FAB spectroscopy and UV spectroscopy, suggests that HF7 is a conjugate of guanosine and one 6-deoxygalactose. Three OH groups in the molecule are derivatives of two sulfates and one acetate.

The coupling constant of anomeric proton of fucose from an ¹H NMR study of HF7 suggests that the linkage of fucose to guanosine to be α in nature and the chemical shift of 4″-H results suggests that the acetate group to be on the 4″-position of fucose.

Taken together all the above information, the structure for HF7 appears to be:

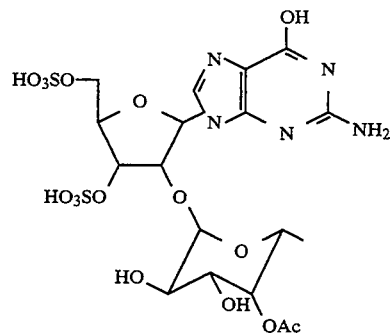

The fucose could be of D or L in configuration and its linkage to ribose could be at either 3′ or 5′ position and either α or β in nature. The sulfate and acetate groups could be on any OH group of HF7.

Synthetic Methods for HF7 and Its analogs

Figure 12:
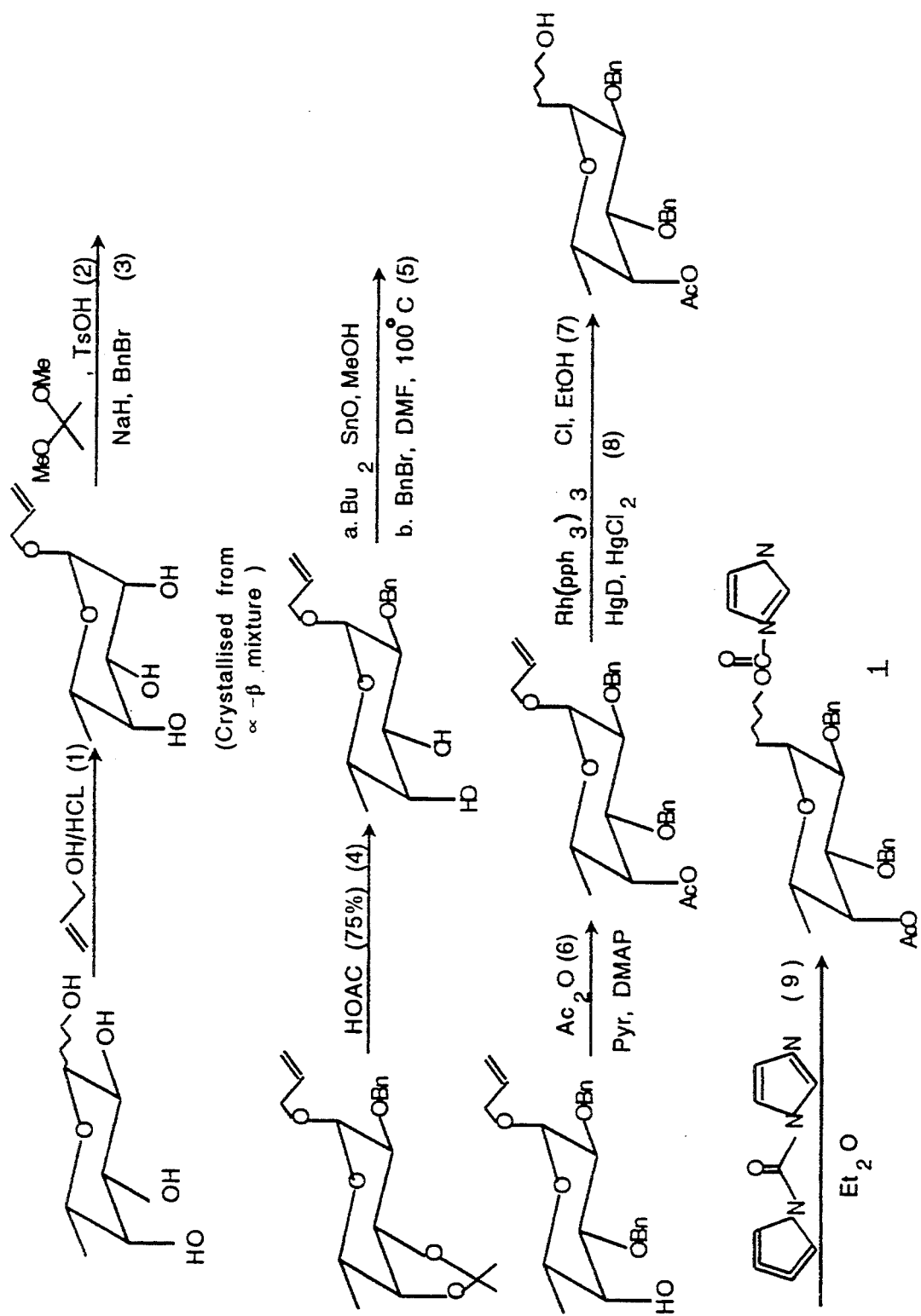
FIGS. 12, 13 and 14 are schemes illustrating how a compound of the present invention can be synthesized.
Figure 13:
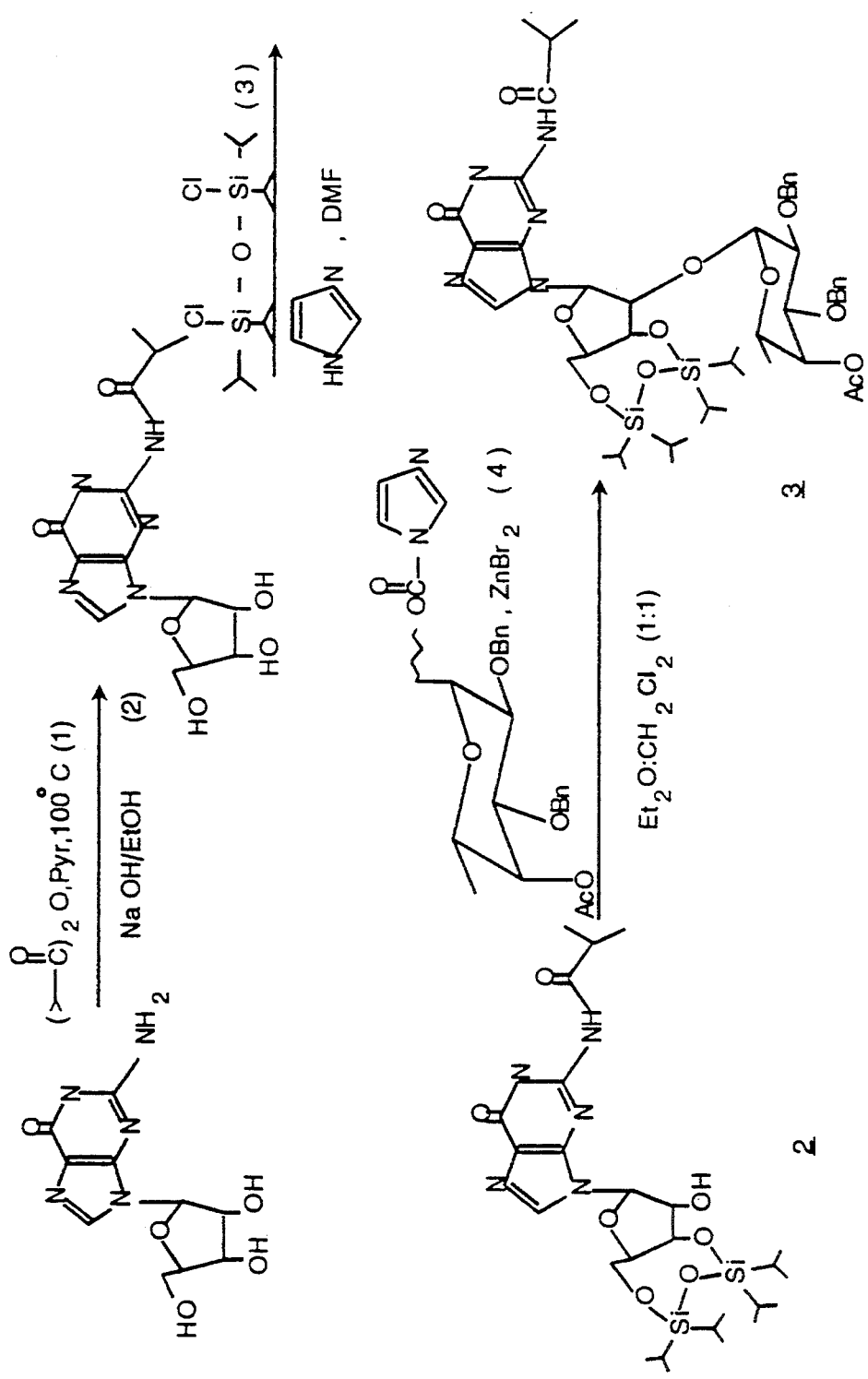
Figure 14:
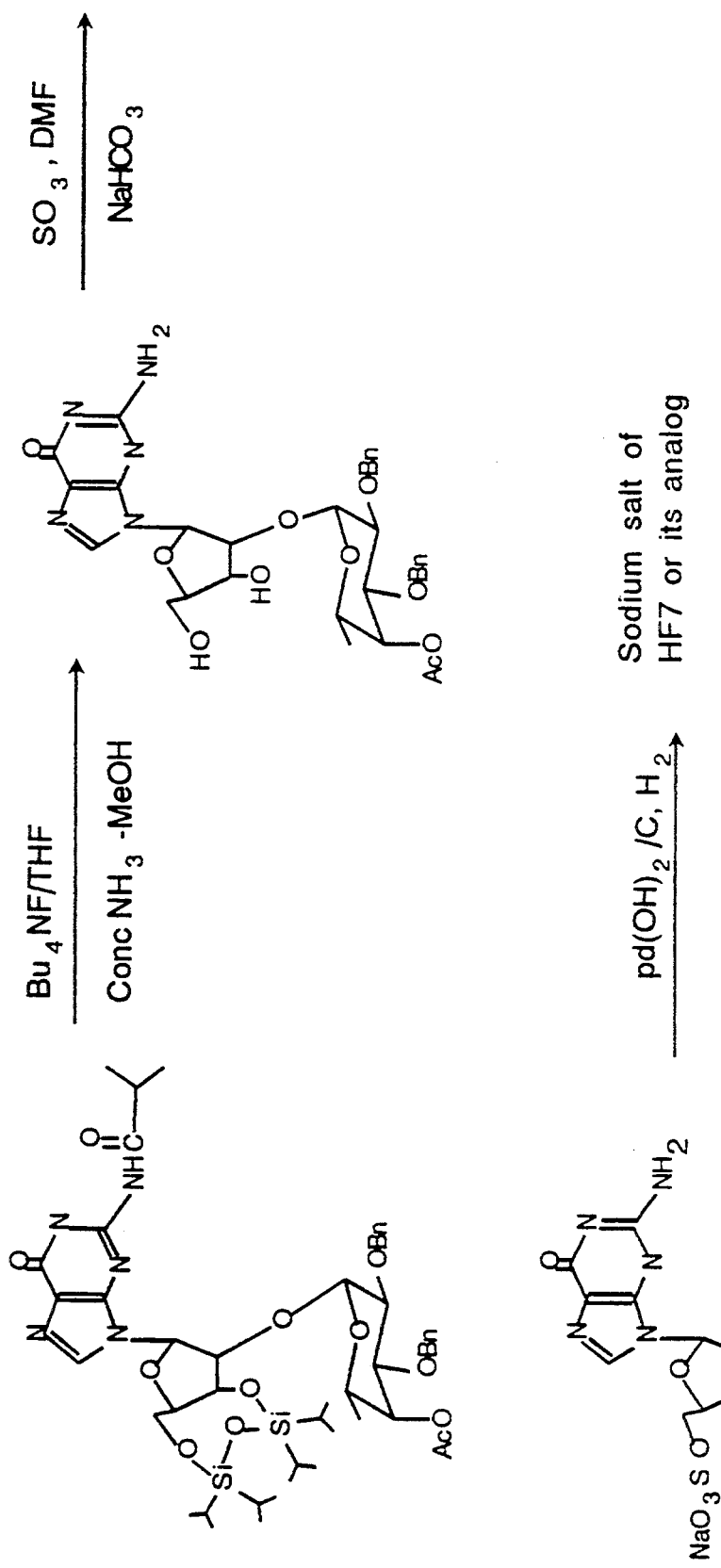

The synthesis of HF7 and/or its analogs can be divided into three parts. First, synthesis of substituted fucose unit; second, synthesis of suitably substituted nucleoside and its coupling to fucose; and, finally, sulfation followed by deprotection. Schemes I, II, and III in FIGS. 12–14 illustrate how HF7 and its analogs can be prepared by synthesis.

(I) Synthesis of substituted D or L fucose

For example, L-fucopyranose was transformed into a 4′-acetyl-2′,3′-O-benzyl-L-fucopyranose following a method described in Dale, J. K. et al., J. Chem. Soc. 52:2534 (1930); and Hockett, R. C. et al., J. Am. Chem. Soc. 61:1658 (1939). See Scheme I in FIG. 12 (DMF=dimethylformamide; DMAP=4-(dimethylamino)pyridine; Bn=benzyl; and pyr=pyridine.). Similarly, D-fucopyranose can be converted to 4′-acetyl-2,3-O-benzyl D-fucopyranose.

The steps in Scheme I can be performed according to the literature methods cited below:

Step (1): Dale, J. K. et al., J. Chem. Sco. 52:2534 (1930); Hockett, R. C. et al., J. Am. Chem. Soc. 61:1658 (1939)

Step (2): Evans, M. E. et al., Carbohydr, Res. 3:453 (1967)

Step (3): Baer, H. H. et al., Carbohydr. Res. 83:146 (1980)

Step (4): Lewbart, M. L. et al., J. Org. Chem. 34:3505 (1969)

Step (5): Nashed, M. A. et al., Carbohydr. Res. 56:419 (1977)

Step (6): Hofle, G. et al., Angew. Chem. Inter. Ed. Engl. 17:569 (1978)

Step (7): Corey, E. J. et al., J. Org. Chem. 38:3224 (1973);

Mario Pinto, B. et al., J. Org. Chem. 55(7):2177 (1990)

Step (8): Mario Pinto, B. et al., J. Org. Chem. 55(7):2177 (1990)

Gigg, R. et al., J. Chem. Soc. C. 1903 (1968)

Step (9): Ford, M. J. et al., Syn Lett. 255 (1990)

(II) Synthesis of suitably substituted nucleotide (Compound 2 in Scheme II) and its coupling to fucose (Compound 1 in Scheme I).

In a typical example, commercially available guanosine was converted into a suitably substituted guanosine as per literature (see steps (1)–(3) below). When the position 4" substituent is OBn in fucose, the glycosylation/coupling reaction (see step (4) below) worked well and the product was completely characterized.

Similarly, any purine- or pyrimidine-based nucleoside can be converted into a suitably protected intermediate (e.g., Compound 2 in Scheme II) which is to be used in the condensation step. It may be required to use different protecting groups based on the nature of the nucleoside to be synthesized.

The steps in Scheme II can be performed according to the literature methods cited below:

Step (1): Reese, C. B. et al., J. Chem. Soc. Perkin I 2937 (1972);
Gait, M. J., "Oligonucleotide Synthesis" p. 168 IRL Press (1984)
Step (2): Ohtsuka, E. et al., Chem. Pharm. Bull.26(10): 2998 (1978)
Step (3): Markiewicz, W. T. J. Chem. Research (S) 24–25 (1979)
Markiewicz, W. T. J. Chem. Research (M) 0181–0196 (1979)
Step (4): Ford, M. J. et al., Syn Lett. 255 (1990)

(III) Sulfation (of Compound 3 in Scheme II) followed by deprotection

Once the glycosylation reaction was completed, the tetraisopropyl disilyl protecting group on the ribose was removed in order to release two OH groups. The protecting group from nucleoside base was then selectively removed and the sulfation was performed per literature method. Finally, the debenzylation resulted in the synthesis of HF7 or its analog. See Scheme III in FIG. 14.

The steps in Scheme III can be performed according to the literature methods cited below:

Step (1): Hanessian, S. et al., Can. J. Chem. 53:2975 (1975)
Step (2): Gait, M. J. Oligenucleotide Synthesis pp. 178 IRL Press (1984)
Step (3): Wolfrom, M. L. et al., J. Am. Chem. Soc. 81:1764, (1959)

Employing the above synthetic strategy, HF7 and its related analogs can be synthesized. For example, one can use different purine or pyrimidine bases or their substituted versions in the nucleoside fragment. Furthermore, one can use L-fucose units (as shown in Schemes I, II and III) or D-fucose units in the glycosylation reactions. In addition, by using different protecting groups in the synthesis, it is possible to place the sulfate or acetate groups on any OH group of ribose and fucose. It is also possible to generate compounds having the fucose on 3' or 5' position of ribose.

OTHER EMBODIMENTS

The foregoing description has been limited to specific embodiments of this invention. It will be apparent, however, that variations and modifications may be made to the invention, with the attainment of some or all of the advantages of the invention.

Other embodiments are within the following claims.

What is claimed is:

1. A compound consisting of a base, a ribose and a fucose, in which said base is a purine, said ribose has $R_1$ and $R_2$ attached respectively to any two of 2'-O, 3'-O and 5'-O, and said fucose has $R_3$, $R_4$ and $R_5$ attached respectively to any three of 1"-O, 2"-O, 3"-O and 4"-O, wherein each $R_1$, $R_2$, $R_3$, $R_4$ and $R_5$ is H, acetate, sulfate, or phosphate; and said base is linked to said ribose via a bond between 9-N of said base and 1'-C of said ribose, and said ribose is linked to said fucose via a bond between any one of 2'-O, 3'-O and 5'-O of said ribose and 1"-C of said fucose.

2. The compound of claim 1, wherein both said ribose and said fucose are of D-configuration.

3. The compound of claim 1, wherein said ribose is of D-configuration and said fucose-is of L-configuration.

4. The compound of claim 2, wherein said ribose is of β-form and said fucose is of α-form.

5. The compound of claim 3, wherein said ribose is of β-form and said fucose is of α-form.

6. The compound of claim 2, wherein both said ribose and said fucose are of β-form.

7. The compound of claim 3, wherein both said ribose and said fucose are of β-form.

8. The compound of claim 1, wherein each $R_1$ and $R_2$ is sulfate.

9. The compound of claim 1, wherein one of $R_3$, $R_4$ and $R_5$ is acetate while each of the other two is H.

10. The compound of claim 9, wherein each $R_1$ and $R_2$ is sulfate.

11. The compound of claim 1, wherein said base is

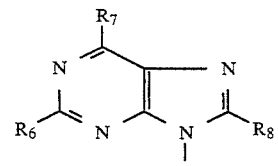

wherein each $R_6$, $R_7$, and $R_8$, is H, hydroxy, acetate, alkyl, aryl, aralkyl, alkaryl, substituted aryl, alkoxy, amino, monoalkylamino, dialkylamino, aminoalkyl, halo, mercapto, acetate, carbamate, thioalkyl, alkanoyl, azido, acetamido, or sulfhydryl.

12. The compound of claim 11, wherein each $R_1$ and $R_2$ is sulfate.

13. The compound of claim 11, wherein one of $R_3$, $R_4$ and $R_5$ is acetate while each of the other two is H.

14. The compound of claim 13, wherein each $R_1$ and $R_2$ is sulfate.

15. The compound of claim 11 wherein $R_6$ is $NH_2$, $R_7$ is OH, and $R_8$ is H.

16. The compound of claim 15, wherein each $R_1$ and $R_2$ is sulfate salt.

17. The compound of claim 15, wherein one of $R_3$, $R_4$ and $R_5$ is acetate while each of the other two is H.

18. The compound of claim 17, wherein $R_1$ and $R_2$ is sulfate.

19. The compound of claim 15, wherein $R_1$ and $R_2$ is hydrogen, sulfate, and each $R_3$, $R_4$ and $R_5$ is H.

20. The compound of claim 1, wherein said base is guanine, adenine, hypoxanthine, 8-azidoadenine, 6-benzylaminopurine, 6-chloropurine, N6-butyryladenine, 8-bromoadenine, 2-chloroadenine, 8-bromoguanine, 6-(methylthio)purine, 2-amino-6-chloropurine, 2-chloro-6-aminopurine, 2-amino-6-mercaptopurine, S-(2-hydroxy-5-nitrobenzyl)-6-thioguanine, or S-(2-hydroxy-5-nitrobenzyl)-6-thiohypoxanthine.

21. The compound of claim 20, wherein each $R_1$ and $R_2$ is sulfate.

22. The compound of claim 20, wherein one of $R_3$, $R_4$ and $R_5$ is acetate while each of the other two is H.

23. The compound of claim 22, wherein each $R_1$ and $R_2$ is sulfate.

24. The compound of claim 1 is guanosine-3′,5′-disulfate-2′-α-D-(4″-acetyl)fucose, guanosine-3′,5′-disulfate-2′-β-D-(4″-acetyl)fucose, guanosine-3′,5′-disulfate-2′-α-L-(4″-acetyl)fucose, or guanosine-3′,5′-disulfate-2′-β-L-(4″-acetyl)fucose.

25. The compound of claim 1 is guanosine-2′,5′-disulfate-3′-α-D-(4″-acetyl)fucose, guanosine-2′,5′-disulfate-3′-β-D-(4″-acetyl)fucose, guanosine-2′,5′-disulfate-3′-α-L-(4″-acetyl)fucose, or guanosine-2′,5′-disulfate-3′-β-L-(4″-acetyl)fucose.

26. The compound of claim 1 is guanosine-3′,5′-disulfate-2′-α-D-(4″-acetyl)fucose.

27. The compound of claim 1 is guanosine-2′,5′-disulfate-3′-(4″-acetyl)fucose.

28. The compound of claim 1 is guanosine-3′,5′-disulfate-2′-β-D-(4″-acetyl)fucose.

29. The compound of claim 1 is guanosine-3′,5′-disulfate-2′-α-L-(4″-acetyl)fucose.

30. The compound of claim 1 is guanosine-3′,5′-disulfate-2′-β-L-(4″-acetyl)fucose.

31. The compound of claim 1 is guanosine-2′,5′-disulfate-3′-β-D-(4″-acetyl)fucose.

32. The compound of claim 1 is guanosine-2′,5′-disulfate-3′-α-L-(4″-acetyl)fucose.

33. The compound of claim 1 is guanosine-2′,5′-disulfate-3′-β-L-(4″-acetyl)fucose.

34. The compound of claim 1 is guanosine-2′,3′-disulfate-5′-α-D-(4″-acetyl)fucose, guanosine-2′,3′-disulfate-5′-β-D-(4″-acetyl)fucose, guanosine-2′,3′-disulfate-5′-α-L-(4″-acetyl)fucose, or guanosine-2′,3′-disulfate-5′-β-L-(4″-acetyl)fucose.

35. The compound of claim 1 is guanosine-2′,3′-disulfate-5′-α-D-(4″-acetyl)fucose.

36. The compound of claim 1 is guanosine-2′,3′-disulfate-5′-β-D-(4″-acetyl)fucose.

37. The compound of claim 1 is guanosine-2′,3′-disulfate-5′-α-L-(4″-acetyl)fucose.

38. The compound of claim 1 is guanosine-2′,3′-disulfate-5′-β-L-(4″-acetyl)fucose.

* * * * *